(12) United States Patent
Gryska et al.

(10) Patent No.: US 10,161,896 B2
(45) Date of Patent: Dec. 25, 2018

(54) SUB-AMBIENT TEMPERATURE VAPOR SENSOR AND METHOD OF USE

(71) Applicant: 3M INNOVATIVE PROPERTIES COMPANY, St. Paul, MN (US)

(72) Inventors: Stefan H. Gryska, Woodbury, MN (US); Michael C. Palazzotto, Woodbury, MN (US); Justin Tungjunyatham, Roseville, MN (US); Myungchan Kang, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 27 days.

(21) Appl. No.: 15/121,326

(22) PCT Filed: Feb. 19, 2015

(86) PCT No.: PCT/US2015/016620
§ 371 (c)(1),
(2) Date: Aug. 24, 2016

(87) PCT Pub. No.: WO2015/130548
PCT Pub. Date: Sep. 3, 2015

(65) Prior Publication Data
US 2017/0016843 A1      Jan. 19, 2017

Related U.S. Application Data

(60) Provisional application No. 61/945,583, filed on Feb. 27, 2014.

(51) Int. Cl.
*G01N 27/22* (2006.01)
(52) U.S. Cl.
CPC ......... *G01N 27/227* (2013.01); *G01N 27/226* (2013.01)

(58) Field of Classification Search
CPC ..... G01N 27/22; G01N 27/221; G01N 27/227
(Continued)

(56) References Cited

U.S. PATENT DOCUMENTS

| 5,792,938 A | 8/1998 | Gokhfeld |
| 7,498,802 B2 | 3/2009 | Takahata |

(Continued)

FOREIGN PATENT DOCUMENTS

| CN | 1176385 A | 3/1998 |
| CN | 102944325 A | 2/2013 |

(Continued)

OTHER PUBLICATIONS

Budd, "Free Volume and Intrinsic Microporosity in Polymers," Journal of Materials Chemistry, 2005, vol. 15, pp. 1977-1986.

(Continued)

*Primary Examiner* — Amy He
(74) *Attorney, Agent, or Firm* — Yufeng Dong (57) ABSTRACT

A vapor sensor comprises a sensor element (110), a cooling member (140), and an operating circuit (160). The sensor element comprises: a first conductive electrode; a second conductive electrode; and a dielectric microporous material at least partially disposed between and contacting the first and second conductive electrodes. The cooling member is in contact with, and configured to cool, the sensor element. The operating circuit is in electrical communication with the first and second conductive electrodes, and is capable of creating a voltage difference between the first and second conductive electrodes such that the sensor element has a capacitance-related property, and monitoring a capacitance-related property of the sensor element. A method of using the vapor sensor to detect an analyte vapor is also disclosed.

20 Claims, 3 Drawing Sheets

(58) Field of Classification Search
USPC .................................. 324/663, 686, 658
See application file for complete search history.

(56) References Cited

U.S. PATENT DOCUMENTS

| | | |
|---|---|---|
| 2006/0246273 A1 | 11/2006 | McKeown |
| 2011/0045601 A1 | 2/2011 | Gryska |
| 2013/0229194 A1 | 9/2013 | Palazzotto |

FOREIGN PATENT DOCUMENTS

| | | |
|---|---|---|
| CN | 103477215 A | 12/2013 |
| CN | 103477216 A | 12/2013 |
| CN | 103528603 A | 1/2014 |
| EP | 2205965 A2 | 7/2010 |
| GB | 2328556 | 2/1999 |
| WO | WO 98/29741 A1 | 7/1998 |
| WO | WO 2005-012397 | 2/2005 |
| WO | WO 2008-008643 | 1/2008 |
| WO | WO 2009-045733 | 4/2009 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2013-090188 | 6/2013 |
| WO | WO 2015-047750 | 4/2015 |

OTHER PUBLICATIONS

Budd, "Polymers of Intrinsic Microporosity (PIMs): Robust, Solution-Processable, Organic Nanoporous Materials," Chemical Communications, 2004, pp. 230-231.

Budd, "Solution-Processed, Organophilic Membrane Derived from a Polymer of Intrinsic Microporosity," Advanced Materials, Mar. 2004, vol. 16, No. 5, pp. 456-459.

Carta, "Novel Spirobisindanes for Use as Precursors to Polymers of Intrinsic Microporosity," Organic Letters, 2008, vol. 10, No. 13, pp. 2641-2643.

Foucaran, "Porous Silicon Layer Coupled With Thermoelectric Cooler: A Humidity Sensor," Sensors and Actuators A: Physical, Feb. 2000, vol. 79, No. 3, pp. 189-193.

Ghanem, "High-Performance Membranes from Polyimides with Intrinsic Microporosity," Advanced Materials, 2008, vol. 20, No. 14, pp. 2766-2771.

Ghanem, "Polymers of Intrinsic Microporosity Derived from Bis(phenazyl) Monomers," Macromolecules, Mar. 2008, vol. 41, No. 5, pp. 1640-1646.

McKeown, "Polymers of Intrinsic Microporosity (PIMs): Bridging the Void between Microporous and Polymeric Materials," Chemistry—A European Journal, Apr. 2005, vol. 11, No. 9, pp. 2610-2620.

"Understanding Thermoelectric Cooling," Active Cool, [retrieved from the internet on Mar. 2, 2014] URL <http://www.activecool.com/technotes/thermoelectric.html> pp. 4.

International Search Report for PCT International Application No. PCT/US2015/016620, dated Jul. 3, 2015, 4 pages.

SUB-AMBIENT TEMPERATURE VAPOR SENSOR AND METHOD OF USE

CROSS REFERENCE TO RELATED APPLICATIONS

This application is a national stage filing under 35 U.S.C. 371 of PCT/US2015/016620, filed Feb. 19, 2015, which claims the benefit of U.S. Application No. 61/945,583, filed Feb. 27, 2014, the disclosure of which is incorporated by reference in its/their entirety herein.

TECHNICAL FIELD

The present disclosure broadly relates to vapor sensors and methods of their use.

BACKGROUND

The presence of vapors, and their concentration in air, is monitored in many fields of endeavor. Various methods for detecting vapors (e.g., volatile organic compounds (VOCs)) have been developed including, for example, photoionization, gas chromatography, gravimetric techniques, spectroscopic techniques (e.g., mass spectrometry, infrared spectroscopy, or fluorescence spectroscopy), and absorptive sensing techniques.

In capacitance sensors, the capacitance of two conductive electrodes (typically parallel or interdigitated), varies as the dielectric constant of material between the two electrodes changes due to the presence of an environmental analyte vapor. Conventional capacitance sensors can be inexpensive to manufacture, but may lack the sensitivity of other more costly techniques.

There is a need for capacitance sensors with improved sensitivity to analyte vapors.

SUMMARY

The present inventors have discovered that by cooling capacitance-type vapor sensors to sub-ambient temperatures the sensitivity of the sensors can be improved. Accordingly, the present disclosure provides capacitance vapor sensors with cooling capability that exhibit markedly enhanced sensitivity (>7 times more sensitive and able to detect analyte vapors on the order of less than one part per million) in operation as compared to equivalent sensors without cooling capability.

In one aspect, the present disclosure provides a vapor sensor comprising:
a sensor element comprising:
  a first conductive electrode;
  a second conductive electrode; and
  a dielectric microporous material at least partially disposed between and contacting the first conductive electrode and the second conductive electrode;
a cooling member in contact with the sensor element, wherein the cooling member is configured to cool the sensor element;
an operating circuit in electrical communication with the first and second conductive electrodes of the sensor element that establishes a voltage difference between the first and second conductive electrodes such that the sensor element has a capacitance-related property, and wherein the operating circuit is capable of monitoring the capacitance-related property of the sensor element.

In another aspect, the present disclosure provides a method of detecting an analyte vapor at an ambient temperature, the method comprising:
providing a vapor sensor according to the present disclosure;
cooling the sensor element to a sub-ambient temperature lower than the ambient temperature;
exposing the microporous material to the analyte vapor; and
measuring the capacitance-related electrical property of the sensor element.

As used herein, the term "capacitance-related property" encompasses any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, conductance, and may be measured according to various methods known in the art.

Features and advantages of the present disclosure will be further understood upon consideration of the detailed description as well as the appended claims.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figure may not be drawn to scale.

DETAILED DESCRIPTION

Figure 1:
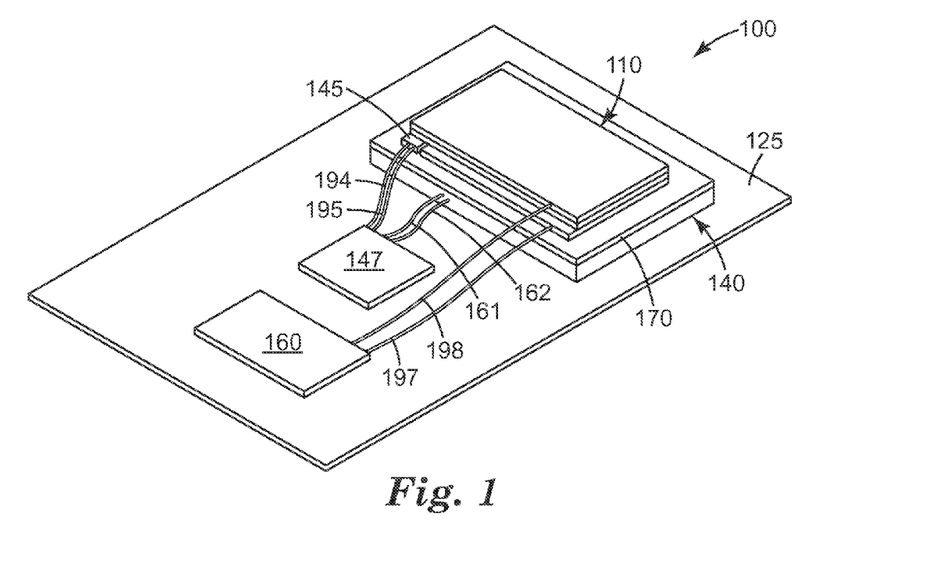
FIG. 1 is a schematic perspective view of an exemplary vapor sensor 100 according to the present disclosure.
Figure 2:
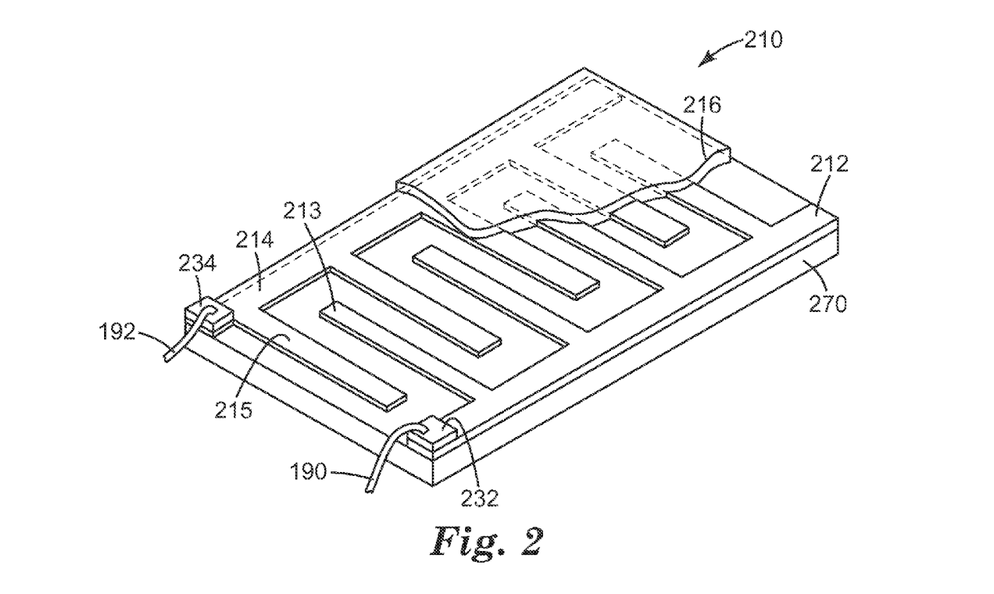
FIG. 2 is a schematic cutaway perspective view of an exemplary sensor element 210 having an interdigitated electrode configuration.
Figure 3:
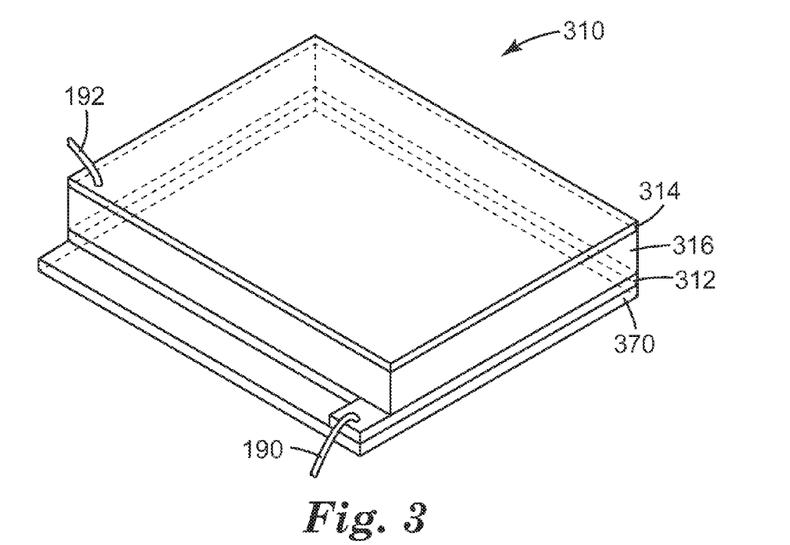
FIG. 3 is a schematic perspective view of an exemplary sensor element 310 having a parallel electrode configuration.

Referring now to FIG. 1, vapor sensor 100 comprises sensor element 110, cooling member 140, and operating circuit 160. Sensor element 110 comprises first and second conductive electrodes and dielectric microporous material disposed between and contacting the first and second conductive electrodes. Two detailed configurations of sensor element 110, showing the first and second electrodes and dielectric microporous material, are shown in FIG. 2 and FIG. 3. Referring to FIGS. 2 and 3, the first conductive electrode (212 or 312) is disposed on optional dielectric base (270 or 370), which is disposed between, and in conductive thermal communication with first conductive electrode (212 or 312) and cooling member 140.

Referring again to FIG. 1, cooling member 140 contacts sensor element 110, and is configured to cool sensor element 110. Operating circuit 160 is in electrical communication with first and second parallel conductive electrodes of sensor element 110 through wires 197, 198. Operating circuit 160 establishes a voltage difference between the first and second conductive electrodes of sensor element 110 such that it has a capacitance-related property (e.g., capacitance). Optional substrate 125 supports operating circuit 160, optional cooling control circuit 147, and cooling member 140. Operating circuit 160 is capable of operating sensor element 110 and monitoring the capacitance-related property. Monitoring may be a discrete intervals or continuously with respect to time. Optional temperature sensor 145 is disposed on dielectric base 170 proximate to cooling member 140. Optional temperature sensor 145 and cooling member 140 are in electrical communication with optional cooling control circuit 147 through respective pairs of wires 194, 195 and 161, 162.

If desired, the vapor sensor may be disposed within a protective housing having an inlet opening such that the vapor sensor is in fluid communication with analyte vapor outside the housing, however this is not a requirement. Design of such an optional housing is within the capability of one of ordinary skill in the art.

Dielectric microporous material is dielectric and microporous. In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the microporous material comprises a so-called Polymer of Intrinsic Microporosity (PIM). PIMs are polymeric materials with nanometer-scale pores due to inefficient packing of the polymer chains. For example, in Chemical Communications, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below).

SCHEME 1

TABLE 1

Further suitable components A and B, and resultant intrinsically microporous polymers, are known in the art; for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Pat. Appl. Publ. No. 2006/0246273 A1 (McKeown et al. Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In addition to solution coating methods, the dielectric microporous material may be applied to the either of the first or second conductive electrodes, or to the optional dielectric base by any other suitable method.

The dielectric microporous material may comprise a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Suitable dielectric bases can comprise any material capable of supporting the first conductive electrode and optionally the second conductive material and dielectric microporous material. The dielectric base may be a continuous slab, layer, or film of material. If present, it is disposed in sufficient proximity to the first conductive electrode that it may serve to provide physical strength and integrity to the sensor element. The dielectric base need not physically contact the first conductive electrode, although this is typically preferable. Any solid material having structural integrity, flexible or rigid, may be used as long as it does not interfere with operation of the sensor element. Suitable dielectric materials that may be used for the dielectric base include, for example, glass, ceramic, and/or plastic. In some embodiments, the substrate has a flat major surface on which the first conductive electrode is disposed. In large-scale production, a polymeric film (such as polyester or polyimide) may be advantageously used.

When a differential voltage is applied across the first and second conductive electrodes, the sensor element functions as a variable capacitor, the capacitance of which changes as a function of the dielectric constant of the dielectric detection material. As the dielectric microporous material contacts an analyte vapor (e.g., an organic analyte vapor), the analyte vapor is adsorbed and/or absorbed in the pores of the dielectric microporous material causing a change in its dielectric constant.

The first conductive electrode can comprise any suitable electrically conductive, and preferably thermally conductive, conductive material. Combinations of different materials (conductive and/or nonconductive) can be used, as different layers or as a mixture, as long as sufficient overall electrical conductivity is provided. The first conductive electrode need not be permeable to the analyte vapor to be detected, however this is not a requirement. Typically, the first conductive electrode has a sheet resistance of less than about $10^7$ ohms/square. Examples of materials that can be used to make the first conductive electrode include, but are not limited to, organic materials, inorganic materials, metals, alloys, and various mixtures and composites comprising any or all of these materials. In certain embodiments, coated (for example, thermal vapor coated, or sputter coated) metals or metal oxides, or combinations thereof, may be used. Suitable conductive materials include for example aluminum, nickel, titanium, tin, indium-tin oxide, gold, silver, platinum, palladium, copper, chromium, and combinations thereof.

The first conductive electrode can be of any thickness as long as it is conductive; for example, it may have a thickness in a range of from at least 4 nanometers (nm) to 1000 nm, or from 10 nm to 200 nm.

In one embodiment, the first conductive electrode is fabricated such that it has elongated fingers that interdigitate with corresponding fingers of the second conductive electrode. Referring now to FIG. 2, sensor element 210 (one exemplary embodiment of sensor element 110) comprises coplanar first and second conductive electrodes 212, 214 having respective interdigitated fingers 213, 215 disposed on dielectric base 270. Dielectric microporous material 216 is disposed over and between (i.e., at least partially between) and contacting first and second conductive electrodes 212, 214. Wires 190 and 192 connect to first and second conductive electrodes 212, 214 via respective electrically conductive bonding pads 232, 234.

In other embodiment, a parallel electrode configuration is used. Referring now to FIG. 3, sensor element 310 (one exemplary embodiment of sensor element 110) comprises first and second conductive electrodes 312,314. First conductive electrode 312 is disposed on optional dielectric base 370. Dielectric microporous material 316 is disposed between and contacts first and second conductive electrodes 312, 314. Wires 190,192 connect to first and second conductive electrodes 312, 314.

The second conductive electrode may include additional components as long as it remains electrically conductive and optionally permeable by at least one organic analyte vapor. In the case of sensor element 310, it is highly preferable that the second conductive electrode be permeable by the analyte vapor to be detected. In the case of sensor element 210 shown in FIG. 2, the second conductive electrode may be permeable or impermeable by the analyte vapor to be detected, since it otherwise does not significantly impede the analyte from interacting with the dielectric microporous material.

Examples of materials that can be used to make the second conductive electrode include organic materials, inorganic materials, metals, alloys, and various mixtures and composites comprising any or all of these materials. In certain embodiments, coated (for example, thermal vapor coated, or sputter coated) metals or metal oxides, or combinations thereof, may be used to form the second conductive electrode such that it is permeable by organic vapors. Suitable conductive materials include for example aluminum, nickel, titanium, tin, indium-tin oxide, gold, silver, platinum, palladium, copper, chromium, carbon nanotubes, and combinations thereof. In certain embodiments, the second conductive electrode is formed by printing a silver ink, followed by drying the ink. Details concerning vapor-deposited second conductive electrodes can also be found in U.S. Pat. Appln. Publ. No. 2013/0229194 A1 (Palazzotto et al.). Combinations of different materials (conductive and/or nonconductive) can be used, as different layers or as a mixture, as long as sufficient overall conductivity and permeability is provided. Typically, the second conductive electrode has a sheet resistance of less than about $10^7$ ohms/square.

The second conductive electrode typically has a thickness in a range of from 1 nm to 100 nm, although other thicknesses may be used. For example, in some embodiments the second conductive electrode may have a thickness in a range of from 1 nm to 3000 nm, or even from 40 nm to 200 nm. Greater thicknesses may have undesirably low levels of permeability, while lesser thicknesses may become insufficiently conductive and/or difficult to electrically connect to the second conductive member. Since the second conductive electrode is permeable, the first conductive electrode typically comprises a continuous, uninterrupted layer, but it may contain openings or other interruptions if desired.

Further details concerning capacitance-related property sensors including a microporous polymer and silver ink-coated second conductive electrodes, and methods for their manufacture can be found, for example, in U.S. Pat. Appl. Publ. No. 2011/0045601 A1 (Gryska et al.), wherein both side-by-side arrangements of the first and second conductive electrodes and parallel plate electrode configurations are discussed. In that implementation, the physical thickness of the detection layer is desirably in a range of from 150 to 1200 nanometers, for example, in a range of from 500 to 900 nanometers, although thinner and thicker detection layers may also be used.

The sensor element may comprise a single capacitive element or a plurality of capacitive elements (e.g., as described in PCT Publ. No. WO 2013/090188 A1 (Gryska et al.) arranged on a single cooling member, for example.

The cooling member may comprise any device capable of cooling the sensor element to a sub-ambient temperature. Examples of suitable device include refrigeration coils, circulating refrigerant in thermally conductive coils, a coolant reservoir (e.g., containing ice, dry ice, or liquid nitrogen), and thermoelectric coolers (e.g., Peltier modules). If electrically operated, the cooling member may be in electrical communication with a cooling control circuit that controls operation of the cooling member. In some embodiments, a temperature sensor is disposed proximate to the sensor element. In such cases, the temperature sensor is preferably in electrical communication with the cooling control circuit, so that the temperature can be effectively regulated.

Figure 4:
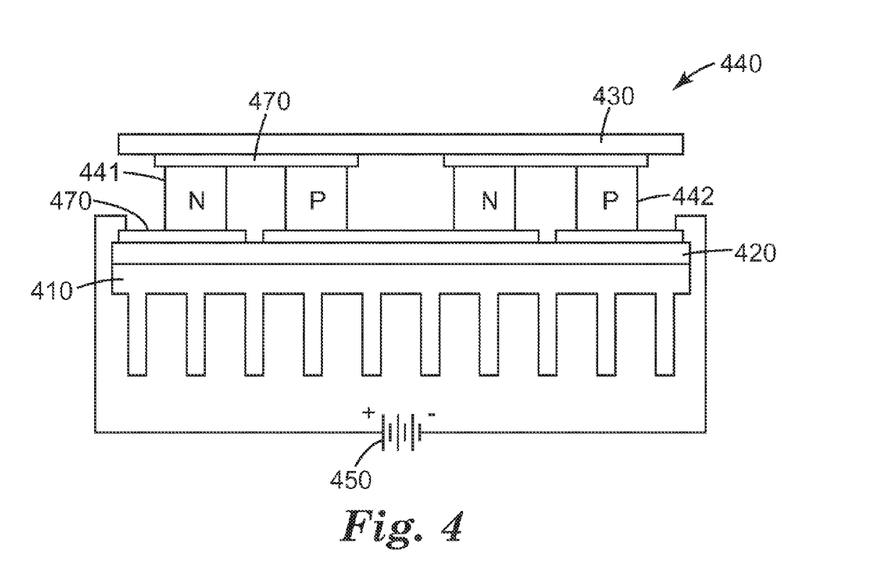
FIG. 4 is a schematic side view of an exemplary cooling member 440 having an interdigitated electrode configuration.

In one embodiment, the cooling member comprises a thermoelectric cooler of the type shown in FIG. 4. Referring now to FIG. 4, thermoelectric cooler 440 comprises heat sink 410; first ceramic member 420 disposed on and in thermal communication with heat sink 410; second ceramic member 430; electrically interconnected (via conductive pads 470) alternating n-type 441 and p-type 442 semiconductors connected electrically in series and thermally in parallel, and sandwiched between first and second ceramic members 420, 430. Direct current (DC) source 450 in cooling control circuit 147 is oriented such that as electrical current passes through the electrically interconnected alternating n-type and p-type semiconductors, first ceramic member 420 is heated and second ceramic member 430 is cooled. By applying a low voltage DC power to the thermoelectric cooler (TEC), heat will be moved through the TEC from the second ceramic member to the first ceramic member where it is transferred to the heat sink and dissipated. Cooling capacity of the thermoelectric cooler is proportional to the magnitude of the applied DC electric current and the thermal conditions on each side of the module. By varying the input current from zero to maximum, it is possible to regulate the heat flow and control the surface temperature.

The first and second ceramic members 420, 430 hold the overall structure together mechanically and electrically insulate the individual elements from one another and from external mounting surfaces. Most commercially available thermoelectric coolers range in size from approximately 2.5 mm to 50 mm square and 2.5 mm to 5 mm in height. A variety of different shapes, metallization patterns and mounting options are commercially available.

Upon absorption of sufficient analyte by the analyte-responsive dielectric layer, a detectable change in an electrical property associated with the sensor element (including but not limited to, capacitance, impedance, admittance, current, or resistance) may occur. Such a detectable change may be detected by an operating circuit 160 that is in electrical communication with the first and second conductive electrodes. In this context, "operating circuit" refers generally to an electrical apparatus that can be used to apply a voltage to the first conductive electrode and the second conductive electrode (thus imparting a charge differential to the electrodes), and/or to monitor an electrical property of the sensor element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

In one embodiment, the operating circuit may comprise a single apparatus which both applies voltage to the conductive electrodes, and monitors an electrical property of the sensor element. In an alternative embodiment, such an operating circuit may comprise two separate apparatuses, one to provide voltage, and one to monitor the signal. The operating circuit may be connected to the first and/or second conductive electrode by wires. In an alternative embodiment, an operating circuit may be provided in direct contact with the first and/or the second conductive electrode, either via connecting devices, or by contacting some portion of the operating circuit directly to an electrically accessible area of each electrode. For example, an operating circuit can be provided that resides on a circuit board or a flexible circuit backing (either of which can also serve as a dielectric base). A first conductive electrode can then be deposited directly onto the circuit board/backing such that it is in direct contact with a portion of the operating circuit.

The operating circuit may include, for example, a power supply (which may comprise a battery or a hardwired power source; alternatively, power may be provided indirectly via, for example, charging of an RFID circuit that is built into the operating circuit). An operating circuit may also include one or more microprocessors configured to control the charging of the electrodes and/or to monitor changes in one or more electrical properties of a charged sensing electrode pair. Also present may be analog-to-digital converters, memory devices for storing data derived from the sensor element, software for operating the sensor element, components that provide data logging and/or one- or two-way telemetry capability, and so on.

Vapor sensors according to the present disclosure are useful for detecting analyte vapors (e.g., volatile organic compounds). To detect and measure an analyte vapor at an ambient temperature, the sensor element of the vapor sensor is cooled to a sub-ambient temperature (i.e., a temperature lower than the ambient temperature where the analyte vapor is to be detected. In some embodiments, sub-ambient temperature is at least 10, at least 20, at least 30, or even at least 40 degrees Celsius lower than the ambient temperature. In some embodiments, the sub-ambient temperature is less than or equal to 0° C., −10° C., −20° C., −30° C. The dielectric microporous material in the vapor sensor is then exposed to the analyte vapor; and at least one electrical property (preferably capacitance) of the sensor element is measured.

Methods of measuring the concentration of an analyte vapor using capacitance-type sensor elements have been previously described. See, for example, PCT Publ. Nos. WO 2013/090188 A1 (Palazzotto et al.) and WO 2012/141894 A1 (Kang et al.).

SELECT EMBODIMENTS OF THE PRESENT DISCLOSURE

In a first embodiment, the present disclosure provides a vapor sensor comprising:
a sensor element comprising:
 a first conductive electrode;
 a second conductive electrode; and
 a dielectric microporous material at least partially disposed between and contacting the first conductive electrode and the second conductive electrode;
a cooling member in contact with the sensor element, wherein the cooling member is configured to cool the sensor element;
an operating circuit in electrical communication with the first and second conductive electrodes of the sensor element that establishes a voltage difference between the first and second conductive electrodes such that the sensor element has a capacitance-related property, and wherein the operating circuit is capable of monitoring the capacitance-related property of the sensor element.

In a second embodiment, the present disclosure provides a vapor sensor according to the first embodiment, further comprising a substrate supporting at least the cooling member and the operating circuit.

In a third embodiment, the present disclosure provides a vapor sensor according to the first or second embodiment, further comprising a dielectric base disposed between the first conductive electrode and the cooling member, wherein the dielectric base is in conductive thermal communication with the first conductive electrode and the cooling member.

In a fourth embodiment, the present disclosure provides a vapor sensor according to the first or second embodiment, wherein the first conductive electrode contacts the cooling member.

In a fifth embodiment, the present disclosure provides a vapor sensor according to any one of the first to fourth embodiments, wherein the cooling member comprises a thermoelectric cooler.

In a sixth embodiment, the present disclosure provides a vapor sensor according to the fifth embodiment, wherein the thermoelectric cooler comprises:
a heat sink;
a first ceramic member disposed on and in thermal communication with the heat sink;
a second ceramic member;
electrically interconnected alternating n-type and p-type semiconductors connected electrically in series and thermally in parallel, and sandwiched between the first and second ceramic members; and
a direct current source, wherein the direct current source is oriented such that as electrical current passes through the electrically interconnected alternating n-type and p-type semiconductors, the first ceramic member is heated and the second ceramic member is cooled.

In a seventh embodiment, the present disclosure provides a vapor sensor according to any one of the first to sixth embodiments, wherein the cooling member is in electrical communication with a cooling control circuit that controls operation of the cooling member.

In an eighth embodiment, the present disclosure provides a vapor sensor according to the seventh embodiment, further comprising a temperature sensor disposed proximate to the sensor element, wherein the temperature sensor is in electrical communication with the cooling control circuit.

In a ninth embodiment, the present disclosure provides a vapor sensor according to any one of the first to eighth embodiments, wherein the second conductive electrode is permeable by at least one organic vapor.

In a tenth embodiment, the present disclosure provides a vapor sensor according to any one of the first to ninth embodiments, wherein the second conductive electrode comprises dried silver ink.

In an eleventh embodiment, the present disclosure provides a vapor sensor according to any one of the first to ninth embodiments, wherein the second conductive electrode comprises a vapor-deposited metal.

In a twelfth embodiment, the present disclosure provides a vapor sensor according to any one of the first to eleventh embodiments, wherein the microporous material comprises a polymer of intrinsic microporosity.

In a thirteenth embodiment, the present disclosure provides a vapor sensor according to any one of the first to twelfth embodiments, wherein the first and second conductive electrodes and the dielectric microporous material are coplanar.

In a fourteenth embodiment, the present disclosure provides a vapor sensor according to any one of the first to twelfth embodiments, wherein the first and second conductive electrodes are parallel.

In a fifteenth embodiment, the present disclosure provides a method of detecting an analyte vapor at an ambient temperature, the method comprising sequentially:

providing a vapor sensor according to any one of the first to fourteenth embodiments;

cooling the sensor element to a sub-ambient temperature lower than the ambient temperature;

exposing the microporous material to the analyte vapor; and measuring the capacitance-related electrical property of the sensor element.

In a sixteenth embodiment, the present disclosure provides a method according to the fifteenth embodiment, wherein the sub-ambient temperature is at least 10 degrees lower than the ambient temperature.

In a seventeenth embodiment, the present disclosure provides a method according to any the fifteenth embodiment, wherein the sub-ambient temperature is at least 20 degrees lower than the ambient temperature.

In an eighteenth embodiment, the present disclosure provides a method according to any one of the fifteenth to seventeenth embodiments, wherein the sub-ambient temperature is less than or equal to zero degrees Celsius.

In a nineteenth embodiment, the present disclosure provides a method according to any one of the fifteenth to seventeenth embodiments, wherein the at least one electrical property comprises capacitance of the sensor element.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of Polymer of Intrinsic Microporosity (PIM) Material:

PIM material was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 5,5',6,6'-tetrahydroxy-3,3,3',3'-tetramethyl-1,1'-spirobisindane (40.000 g) was combined with 23.724 g of tetrafluoroterephthalonitrile, 97.373 g of potassium carbonate, and 1016.8 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from methanol, and air dried at room temperature. A yellow solid product was obtained having a number-average molecular weight of approximately 41900 g/mol, as determined by gel permeation chromatography analysis using light scattering detection.

Preparation of Sensors Elements:

Sensor elements were prepared on PGO glass slides (glass number 0050-0050-0010-GF-CA, 50 mm×50 mm, 1.1 mm thick, material C-263, surface 80/50, obtained from Precision Glass & Optics of Santa Ana, Calif.), which were cleaned by soaking them in LIQUI-NOX detergent solution (obtained from Alconox, Inc., White Plains, N.Y.) for 30 to 60 minutes, then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 7.6 cm (3 inch) wafer carriers obtained from Entegris, Chaska, Minn.

A first conductive electrode was deposited onto the PGO glass slide by thermally vapor coating 10.0 nm of titanium (obtained as titanium slug, 9.5 mm×9.5 mm, 99.9+% purity from Alfa Aesar, Ward Hill, Mass.) at a rate of 0.1 nm per second (nm/sec) followed by 100.0 nm of nickel (obtained as 3.175 mm×3.175 mm slug, 99.995% pure from Alfa Aesar) at 0.1 nm/sec using a square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 1.16 mm thick stainless steel. The deposition process was controlled using an INFICON XTC/2 THIN FILM DEPOSITION CONTROLLER from INFICON of East Syracuse, N.Y.

A PIM solution of 5.6 percent by weight in chlorobenzene was prepared by mixing the components in a small jar and placing it on a roller mill (Mini Bottle Roller number 348920 from Wheaton Science Products, Millville, N.J.) for about 3 hours, then filtering through an ACRODISC 25 MM SYRINGE FILTER WITH 1 MICRON GLASS FIBER MEMBRANE filter disk from PALL Life Sciences, Ann Arbor, Mich. The solution was allowed to sit over night so that any bubbles that formed could escape.

The PIM solution was then used in the preparation of all sensor specimens. To coat a specimen, it was placed in the spin coater and about 0.5 ml of chlorobenzene was placed on the sample. Each specimen was spun for 15 seconds at 300 rpm then 45 seconds at 2000 rpm. The solvent was dispensed during the first 15 seconds of the spin coating profile. Then, for all specimens, about 1 mL of PIM solution was dispensed during the first 15 seconds while the specimen was spinning A spin profile of 15 seconds at 300 rpm then 45 seconds at 2000 rpm was used for all samples. After spin coating, PIM thickness measurements were made using a Model XP-1 Profilometer from AMBiOS Technology of Santa Cruz, Calif. All samples were baked for 1 hour at 100° C. after coating.

A 2 inches (5 cm)×2 inches (5 cm) mask (MASK B) having a 2×2 regular array of four 0.60 inch (1.5 cm)

height×0.33 inch (0.84 cm) width rectangular openings vertically separated by 0.22 inch (0.56 cm) and horizontally separated by 0.48 inch (1.2 cm) was made from 24 gauge stainless steel by laser milling. The second conductive electrode was vapor deposited through MASK B using thermal deposition of gold (obtained as metal spatters, 99.999% typical purity from Cerac Inc., Milwaukee, Wis.) at 6 nm thickness.

The second conductive electrode was vapor deposited through a 24 gauge stainless steel LATE mask using thermal deposition of gold at 6 nm thickness. After depositing the active electrode, a connecting electrode was deposited by thermal vapor coating 10.0 nm of titanium (obtained as titanium slug, 9.5 mm×9.5 mm, 99.9+% purity from Alfa Aesar) followed by 150.0 nm of aluminum (Aluminum shot, 4-8 mm, Puratronic 99.999% from Alfa Aesar) through a 24 gauge stainless steel mask (MASK C). MASK C was 2 inches (5 cm)×2 inches (5 cm) mask and had two horizontal rectangular openings with a height of 0.4 inch (1 cm), left and right borders of 0.14 inch (0.36 cm), and a separation of 0.92 inch (2.4 cm), prepared by laser milling from 24 gauge stainless steel. The deposition process was controlled using an INFICON XTC/2 THIN FILM DEPOSITION CONTROLLER.

This sensor production process produced a set of 4 sensor elements of approximately 5 mm×6 mm active area (area under the overlapping top and bottom electrodes that was not covered by the connecting electrode) on an approximately 50 mm×50 mm glass substrate. Individual sensor elements were produced by dicing the sample using a standard glass scoring cutter on the back (inactive side) while supporting the sensor elements so that their front (active) surfaces would not be damaged. After dicing, the individual sensor elements were tested for electrical shorts using a Protek multimeter.

All tests were performed in air that had been passed over DRIERITE calcium sulfate desiccant to remove moisture, and passed over activated carbon to eliminate any organic contaminants.

Capacitance Measurement Method:

Before testing, vapor sensors (prepared as described below) were baked at 150° C. for 15 minutes using a convection oven. All tests were performed in air that had been passed over a calcium sulfate desiccant (obtained as DRIERITE from W. A. Hammond Drierite Co. Ltd., Xenia, Ohio) to remove moisture, and passed over activated carbon (obtained as KURARAY GG 12×20 from Kuraray Chemical Co., Ltd., Osaka, Japan") to eliminate any organic contaminates. Various VOC solvent vapor levels were generated using a 10 L/minute dry air flow through the system and a syringe pump (available as KD SCIENTIFIC SYRINGE PUMP from KD Scientific Inc. of Holliston, Mass.) fitted with a 500-microliter gas-tight syringe (obtained from Hamilton Company of Reno, Nev.). The syringe pump delivered the VOC solvent onto a piece of filter paper suspended in a 500 ml three-necked flask. The flow of dry air passed over the paper and vaporized the solvent. Delivery of the solvent at different rates by controlling the syringe pump generated different concentrations of vapor. The syringe pump was controlled by a LABVIEW (software available from National Instruments of Austin, Tex.) program that allowed vapor profiles to be generated during a test run. In some circumstances (using a set of flow meters from Omega Engineering, Inc., Stamford, Conn.), fraction of the vapor stream was diluted with dry air to generate very low concentrations of the analyte. A MIRAN IR ANALYZER (available from Thermo Fischer Scientific, Inc. of Waltham, Mass.) was used to verify the vapor concentrations. The capacitance and dissipation factors were measured with an LCR meter (available as INSTEK MODEL 821 LCR METER from Instek America Corp., Chino, Calif.) applying one volt at 1000 Hz across the conductive first and second conductive electrodes.

This data was collected and stored using the same LABVIEW program that controlled the syringe pump. The testing was done in a test chamber that contained a Peltier MODULE CP85338 (available from Digi-Key Corporation, Thief River Falls, Minn.) and a capacitive sensor. During the testing, the temperature of the Peltier module was controlled by the single output DC power supply (available under the designation 1735A from Fotronic Corporation, Melrose, Mass.). The back of the sensor remained in constant contact with the top surface of the Peltier module for the duration of the experiment. The bottom surface of Peltier module was in contact with water-cooled copper block heat sink to enhance the cooling capability of the system.

Capacitance measurements for a given solvent at a specified temperature were reported in the form of $\Delta C/C_O$ versus concentration, wherein $C_O$ is the sensor element baseline capacitance at the specified temperature in the absence of analyte vapor, and $\Delta C = (C_{measured}) - C_O$, where $(C_{measured})$ is the measured capacitance in the presence of analyte vapor at the specified temperature.

Comparative Example A

Figure 5:
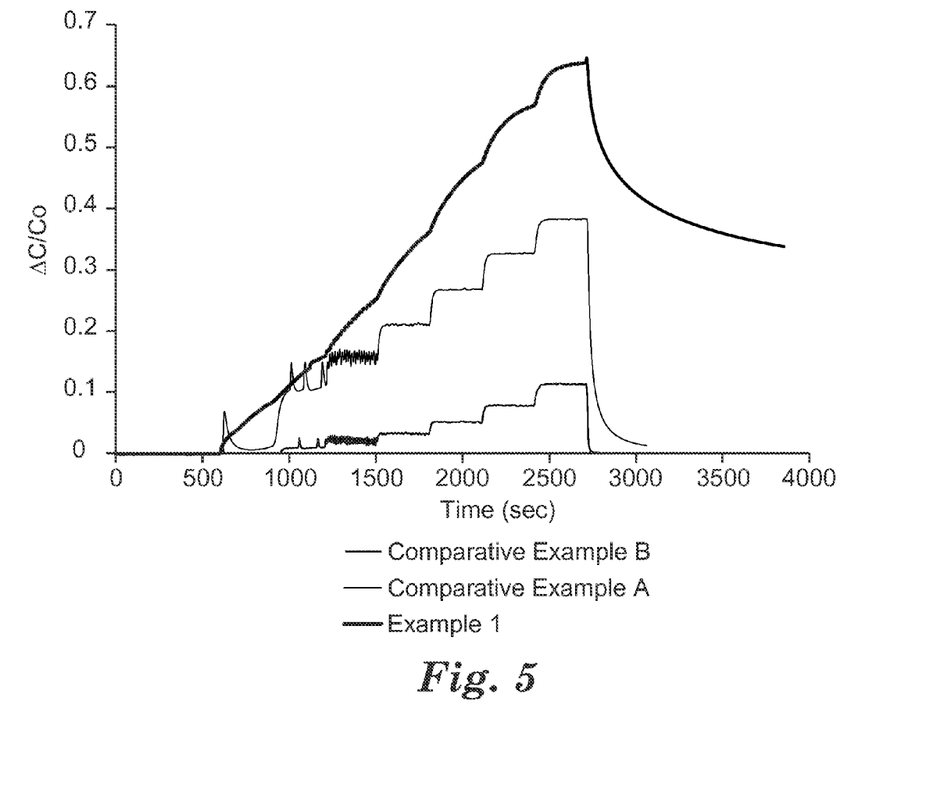
FIG. 5 is a plot of $\Delta C/C_O$ vs. vapor exposure time for Example 1 and Comparative Examples A and B.

A sensor element was prepared according to the Preparation of Sensor Elements procedure and tested according to the Capacitance Measurement Method. Before testing, the sensor element was heated for 15 minutes at 150° C. in an oven. Capacitance measurements were made with methyl ethyl ketone (MEK) vapor in dry air at 6, 12, 25, 50, 100, 200 and 400 parts per million (ppm) with 5 minutes exposure time for each concentration at an ambient temperature of 22° C. MEK exposure showed good sensor sensitivity and good kinetics over a wide range of concentration. Results are reported in the form of $\Delta C/C_O$ versus concentration in Table 2 and FIG. 5.

Comparative Example B

A sensor element was prepared according to the Preparation of Sensor Elements procedure and tested according to the Capacitance Measurement Method. Before testing, the sensor element was heated for 15 minutes at 150° C. in an oven. Capacitance measurements were made with MEK vapor in dry air at 6, 12, 25, 50, 100, 200 and 400 parts per million (ppm) with 5 minutes exposure time for each concentration at an elevated temperature of 60° C. Results are reported in the form of $\Delta C/C_O$ versus concentration in Table 2 and FIG. 5.

Example 1

A sensor element was prepared according to the Preparation of Sensor Elements procedure and tested according to the Capacitance Measurement Method. Before testing, the sensor element was heated for 15 minutes at 150° C. in an oven. Capacitance measurements were made with MEK vapor in dry air at 6, 12, 25, 50, 100, 200 and 400 parts per million (ppm) with 5 minutes exposure time for each concentration at a sub-ambient temperature of −6° C. Results are reported in the form of $\Delta C/C_O$ versus concentration in Table 2 and FIG. 5.

TABLE 2

| | COMPARATIVE EXAMPLE A | COMPARATIVE EXAMPLE B | EXAMPLE 1 |
|---|---|---|---|
| TEST TEMPERATURE | 22° C. | 60° C. | −6° C. |
| MEK CONCENTRATION, ppm | | $\Delta C/C_O$ | |
| 6 | 0.010 | 0 | 0.080 |
| 12 | 0.108 | 0.010 | 0.155 |
| 25 | 0.159 | 0.016 | 0.246 |
| 50 | 0.211 | 0.031 | 0.355 |
| 100 | 0.268 | 0.052 | 0.468 |
| 200 | 0.327 | 0.078 | 0.565 |
| 400 | 0.384 | 0.113 | 0.630 |

Examples 2 to 5 and Comparative Examples C-f

For each of Examples 2 to 5 and Comparative Examples C-F, the sensor elements were prepared and tested as in Example 1, except that the capacitance measurement was made at a single vapor concentration using the solvents and temperatures indicated in Table 3. For each of Examples 2 to 5 and Comparative Examples C-F, the capacitance measurement results are reported in Table 3.

Comparative Example C

A sensor element was prepared and tested according to the Preparation of Sensors and Capacitance Measurement Method. Before testing, the sensor was heated for 15 minutes at 150° C. in an oven. Capacitance measurement was made with isopropyl alcohol (IPA) vapor in dry air at 1 part per million (ppm) for 5 minutes of exposure time at an ambient temperature of 18.6° C. Results are reported in Table 3.

Example 2

A sensor element was prepared and tested according to the Preparation of Sensors and Capacitance Measurement Method. Before testing, the sensor element was heated for 15 minutes at 150° C. in an oven. Capacitance measurement was made with isopropanol (IPA) vapor in dry air at 1 ppm with 5 minutes through the exposure time at a sub-ambient temperature of −13.0° C. Results are reported in Table 3.

COMPARATIVE EXAMPLE D sensor element was prepared and tested according to the Preparation of Sensors and Capacitance Measurement Method. Before testing, the sensor element was heated for 15 minutes at 150° C. in an oven. Capacitance measurement was made with methanol vapor in dry air at 1 ppm with 5 minutes through the exposure time at an ambient temperature of 17.6° C. Results are reported in Table 3.

Example 3

A sensor element was prepared and tested according to the Preparation of Sensors and Capacitance Measurement Method. Before testing, the sensor element was heated for 15 minutes at 150° C. in an oven. Capacitance measurement was made with methanol vapor in dry air at 1 ppm with 5 minutes through the exposure time at a sub-ambient temperature of −10.0° C. Results are reported in Table 3.

COMPARATIVE EXAMPLE E sensor element was prepared and tested according to the Preparation of Sensors and Capacitance Measurement Method. Before testing, the sensor element was heated for 15 minutes at 150° C. in an oven. Capacitance measurement was made with ethanol vapor in dry air at 1 ppm with 5 minutes through the exposure time at an ambient temperature of 18.9° C. Results are reported in Table 3.

Example 4

A sensor element was prepared and tested according to the Preparation of Sensors and Capacitance Measurement Method. Before testing, the sensor element was heated for 15 minutes at 150° C. in an oven. Capacitance measurement was made with ethanol vapor in dry air at 1 ppm with 5 minutes through the exposure time at a sub-ambient temperature of −11.4° C. Results are reported in Table 3.

COMPARATIVE EXAMPLE F sensor element was prepared and tested according to the Preparation of Sensors and Capacitance Measurement Method. Before testing, sensor element was heated for 15 minutes at 150° C. in an oven. Capacitance measurement was made with ethyl acetate vapor in dry air at 500 parts per billion (ppb) with 5 minutes through the exposure time at an ambient temperature of 21.1° C. Results are reported in Table 3.

Example 5

A sensor element was prepared and tested according to the Preparation of Sensors and Capacitance Measurement Method. Before testing, sensor was heated for 15 minutes at 150° C. in an oven. Capacitance measurement was made with Ethyl Acetate vapor in dry air at 500 parts per billion (ppb) with 5 minutes through the exposure time at a sub-ambient temperature of −18.3° C. Results are reported in Table 3.

TABLE 3

| | | | ROOM TEMPERATURE EXPERIMENT | | LOW TEMPERATURE EXPERIMENT | |
|---|---|---|---|---|---|---|
| EXAMPLE | VOC | CONCENTRATION, ppm | $\Delta C/C_0$ | Actual Temperature, ° C. | $\Delta C/C_0$ | Actual Temperature, ° C. |
| COMPARATIVE EXAMPLE C | IPA | 1 | $1.09 \times 10^{-4}$ | 18.6 | | |
| 2 | IPA | 1 | | | $8.96 \times 10^{-4}$ | −13.0 |
| COMPARATIVE EXAMPLE D | methanol | 1 | $3.62 \times 10^{-5}$ | 17.6 | | |
| 3 | methanol | 1 | | | $1.86 \times 10^{-3}$ | −10.0 |
| COMPARATIVE EXAMPLE E | ethanol | 1 | $1.53 \times 10^{-4}$ | 18.9 | | |
| 4 | ethanol | 1 | | | $1.82 \times 10^{-3}$ | −11.4 |

TABLE 3-continued

| EXAMPLE | VOC | CONCENTRATION, ppm | ROOM TEMPERATURE EXPERIMENT | | LOW TEMPERATURE EXPERIMENT | |
|---|---|---|---|---|---|---|
| | | | $\Delta C/C_0$ | Actual Temperature, °C. | $\Delta C/C_0$ | Actual Temperature, °C. |
| COMPARATIVE EXAMPLE F | ethyl acetate | 0.5 | $3.99 \times 10^{-4}$ | 21.1 | | |
| 5 | ethyl acetate | 0.5 | | | $2.75 \times 10^{-3}$ | −18.3 |

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A vapor sensor comprising:
   a sensor element comprising:
     a first conductive electrode;
     a second conductive electrode; and
     a dielectric microporous material at least partially disposed between and contacting the first conductive electrode and the second conductive electrode, the dielectric microporous material comprising a polymer of intrinsic microporosity (PIM) as an absorptive dielectric material where an organic analyte vapor is adsorbed to cause a change of a dielectric constant of the dielectric microporous material;
   a cooling member in contact with the sensor element, wherein the cooling member is configured to cool the sensor element;
   an operating circuit in electrical communication with the first and second conductive electrodes of the sensor element that establishes a voltage difference between the first and second conductive electrodes such that the sensor element has a capacitance-related property, and wherein the operating circuit is capable of monitoring the capacitance-related property of the sensor element.

2. The vapor sensor of claim 1, further comprising a substrate supporting at least the cooling member and the operating circuit.

3. The vapor sensor of claim 1, further comprising a dielectric base disposed between the first conductive electrode and the cooling member, wherein the dielectric base is in conductive thermal communication with the first conductive electrode and the cooling member.

4. The vapor sensor of claim 1, wherein the first conductive electrode contacts the cooling member.

5. The vapor sensor of claim 1, wherein the cooling member comprises a thermoelectric cooler.

6. The vapor sensor of claim 5, wherein the thermoelectric cooler comprises:
   a heat sink;
   a first ceramic member disposed on and in thermal communication with the heat sink;
   a second ceramic member;
   electrically interconnected alternating n-type and p-type semiconductors connected electrically in series and thermally in parallel, and sandwiched between the first and second ceramic members; and
   a direct current source, wherein the direct current source is oriented such that as electrical current passes through the electrically interconnected alternating n-type and p-type semiconductors, the first ceramic member is heated and the second ceramic member is cooled.

7. The vapor sensor of claim 1, wherein the cooling member is in electrical communication with a cooling control circuit that controls operation of the cooling member.

8. The vapor sensor of claim 7, further comprising a temperature sensor disposed proximate to the sensor element, wherein the temperature sensor is in electrical communication with the cooling control circuit.

9. The vapor sensor of claim 1, wherein the second conductive electrode is permeable by at least one organic vapor.

10. The vapor sensor of claim 1, wherein the second conductive electrode comprises dried silver ink.

11. The vapor sensor of claim 1, wherein the second conductive electrode comprises a vapor-deposited metal.

12. The vapor sensor of claim 1, wherein the first and second conductive electrodes and the dielectric microporous material are coplanar.

13. The vapor sensor of claim 1, wherein the first and second conductive electrodes are parallel.

14. The vapor sensor of claim 1, wherein the PIM is hydrophobic, and the sensor element is relatively insensitive to the presence of water as compared to the organic analyte vapor.

15. A method of detecting an organic analyte vapor at an ambient temperature, the method comprising sequentially:
   providing a vapor sensor according to claim 1;
   cooling the sensor element to a sub-ambient temperature lower than the ambient temperature;
   exposing the microporous material to the organic analyte vapor; and
   measuring the capacitance-related electrical property of the sensor element.

16. The method of claim 15, wherein the sub-ambient temperature is at least 10 degrees lower than the ambient temperature.

17. The method of claim 15, wherein the sub-ambient temperature is at least 20 degrees lower than the ambient temperature.

18. The method of claim 15, wherein the sub-ambient temperature is less than or equal to zero degrees Celsius.

19. The method of claim 15, wherein the at least one electrical property comprises capacitance of the sensor element.

20. The method of claim 15, wherein the cooling enhances a sensitivity of the vapor sensor by greater than 7 times and allow the vapor sensor to detect the organic analyte vapor on the order of less than one part per million.

* * * * *

UNITED STATES PATENT AND TRADEMARK OFFICE
CERTIFICATE OF CORRECTION

PATENT NO. : 10,161,896 B2
APPLICATION NO. : 15/121326
DATED : December 25, 2018
INVENTOR(S) : Stefan Gryska et al.

It is certified that error appears in the above-identified patent and that said Letters Patent is hereby corrected as shown below:

In the Specification

Column 12
Line 59, Delete "spinning" and insert -- spinning. --, therefor.

Column 15
Line 16 (Approx.), Delete "-f" and insert -- -F --, therefor.

Columns 15-16 (Table 3)
Line 56 (Approx.), Delete "$\Delta C/C_0$" and insert -- $\Delta C/C_O$ --, therefor.
Line 56 (Approx.), Delete "$\Delta C/C_0$" and insert -- $\Delta C/C_O$ --, therefor.

Columns 17-18 (TABLE 3)
Line 6 (Approx.), Delete "$\Delta C/C_0$" and insert -- $\Delta C/C_O$ --, therefor.
Line 6 (Approx.), Delete "$\Delta C/C_0$" and insert -- $\Delta C/C_O$ --, therefor.

Signed and Sealed this
Twelfth Day of November, 2019

Andrei Iancu
*Director of the United States Patent and Trademark Office*